United States Patent [19]

Campbell et al.

[11] Patent Number: 4,520,025

[45] Date of Patent: May 28, 1985

[54] BICYCLIC NITROGEN HETEROCYCLIC ETHERS AND THIOETHERS, AND THEIR PHARMACEUTICAL USES

[75] Inventors: Henry F. Campbell, Lansdale; Donald E. Kuhla, Doylestown; William L. Studt, Harleysville; Stuart A. Dodson, Lansdale, all of Pa.

[73] Assignee: William H. Rorer, Inc., Fort Washington, Pa.

[21] Appl. No.: 400,350

[22] Filed: Jul. 21, 1982

[51] Int. Cl.³ .................. C07D 217/24; A61K 31/47
[52] U.S. Cl. .................. 514/275; 546/139; 546/141; 546/142; 546/143; 546/145; 546/148; 544/128; 544/321; 544/363; 514/307; 514/309; 514/310
[58] Field of Search .............. 546/139, 141, 142, 143, 546/145, 148; 544/128, 321, 363; 424/251, 258

[56] References Cited

U.S. PATENT DOCUMENTS

| | | | |
|---|---|---|---|
| 4,318,913 | 3/1982 | Clitherow | 424/267 |
| 4,337,256 | 6/1982 | Suzuki | 548/135 |
| 4,338,328 | 7/1982 | White | 424/269 |
| 4,374,248 | 2/1983 | Crenshaw | 548/135 |
| 4,380,639 | 4/1983 | Crenshaw | 548/135 |
| 4,442,110 | 4/1984 | Clitherow | 424/263 |

FOREIGN PATENT DOCUMENTS

| | | | |
|---|---|---|---|
| 2506764 | 12/1982 | France | 424/263 |
| 58-18366 | 2/1983 | Japan | 424/263 |
| 2065121 | 6/1981 | United Kingdom . | |

*Primary Examiner*—Robert Gerstl
*Attorney, Agent, or Firm*—James A. Nicholson; Alexis Barron; Martin F. Savitzky

[57] ABSTRACT

A class of bicyclic nitrogen heterocyclic ether and thioether compounds exhibiting pharmacological activity including anti-secretory and anti-ulcerogenic activity, pharmaceutical compositions comprising these compounds, and methods for the treatment of gastrointestinal hyperacidity and ulcerogenic disorders in mammals using said compositions are disclosed.

17 Claims, No Drawings

BICYCLIC NITROGEN HETEROCYCLIC ETHERS AND THIOETHERS, AND THEIR PHARMACEUTICAL USES

FIELD OF THE INVENTION

This invention relates to a class of bicyclic heterocyclic compounds characterized by an ether or thioether substituent on the bicyclic ring system and methods for the treatment of physiological disorders, including gastrointestinal disorders, such as peptic ulcer, in humans and other mammals.

BACKGROUND OF THE INVENTION

The treatment of peptic ulcer has changed in the last few years to include the use of anti-secretory agents which selectively block histamine $H_2$-receptors. The subdivision of histamine receptors into two groups, the $H_1$- and $H_2$-receptors, was proposed by Ash and Schild (Brit. J. Pharmacol. Chemother, 1966, 27, 427) and Black et al (Nature 1972, 236, 385). The $H_1$-receptor is involved in the bronchial and gastrointestinal smooth muscle stimulative action of histamine. Drugs which block this action are labelled "antihistamines" (e.g. mepyramine). Black et al, cited above, described the group of substances which act at histamine receptors other than the $H_1$-receptor as the $H_2$-receptors. Blocking the action of histamine at the $H_2$-receptors will selectively block histamine's stimulative action on gastric acid secretion and heart rate. Burimamide was the first clinically effective $H_2$-receptor antagonist inhibiting gastric secretion in man, but its oral absorption is poor. Subsequent studies developed the orally active Metiamide, the side effects of which limited clinical use, and Cimetidine which has been marketed as an anti-ulcer drug. A number of classes of heterocyclic chemical compounds have been reported as $H_2$-receptor antagonists, for example, those disclosed in U.S. Pat. Nos. 4,104,381, 4,279,819, 4,323,566, and British published patent application GB 2067987A, the disclosures of which are incorporated by reference.

Another method for the prevention or treatment of gastric ulcer comprises the use of drugs which neither neutralize nor inhibit the secretion of gastric acid. These drugs are described as "cytoprotective" agents and constitute a class of anti-ulcer compounds which function to enhance the normal defense mechanisms of the body, rather than to reduce normal body secretions. Prostaglandins have been implicated in the mechanism of cytoprotection by a number of workers in the field. See, the discussion of cytoprotection in Robert, Andre, "Prostaglandins and Digestive Diseases", *Advances in Prostaglandin and Thromboxane Research*, Vol. 8 (Raven Press, N.Y. 1980), and Robert et al, "Cytoprotection by Prostaglandins in Rats", *Gastroenterology*, 77, 433–443 (1979), hereby incorporated by reference. Drugs, other than prostaglandins, which exhibit cytoprotective activity include carbenoxolone sodium, reported to exhibit undesirable side effects, such as edema, diastolic hypertension or hypokalemia, and the thiazol-2-yl-carbamoylcarboxylic acids, esters and imides described in U.S. Pat. No. 4,321,372.

The compounds of the present invention are a class of novel bicyclic heterocyclics which exhibit anti-secretory activity as $H_2$-receptor antagonists and cytoprotective activity.

SUMMARY OF THE INVENTION

This invention comprises a class of compounds according to Formula I $$\underset{R_1}{\overset{W_2-(W_3)_c}{\underset{N-(W_1)_b}{\diagup}}}\overset{X}{\underset{Y}{\diagdown}}-(CH_2)_a-Z-(CH_2)_f-NH-R_2 \quad I$$

wherein:

$W_1$, $W_2$ and $W_3$ are independently CH, $CH_2$, $CHR_3$ or $CR_3$;

X is N or CH, or $(CH)_{3-d}$, when Y is $(CH)_d$;

Y is O, S, or $NR_4$, or $(CH)_d$, when X is $(CH)_{3-d}$;

Z is O, S, $$\downarrow_{O}^{S}, \quad \diagup_{O}^{S}\diagdown_{O},$$

or $CH_2$;

and wherein:

$R_1$ is H, alkyl, acyl, haloalkyl, alkoxy alkyl, hydroxyalkyl, aminoalkyl, mono- and di-alkylamino alkyl, or together with $W_1$ forms a carbon-nitrogen double bond;

$R_2$ is selected from the group consisting of H, $$\underset{-C-NHR_5,}{\overset{N-CN}{\parallel}} \quad \underset{-C-S-alkyl,}{\overset{N-CN}{\parallel}}$$

$$\underset{N}{\overset{R_5}{\diagdown}}\underset{\diagdown}{\overset{N-N}{\diagup}}-NHR_6, \quad \underset{-C-NHR_5,}{\overset{CH-NO_2}{\parallel}}$$

$$\underset{NHR_5}{\overset{N-S(O)_e}{\diagdown}}\underset{N}{\diagup}, \text{ and } \underset{H}{\overset{O}{\diagdown}}\underset{N}{\overset{\parallel}{\diagup}}\text{alkaryl};$$

$R_3$ is alkyl, halo, alkoxy, hydroxy, hydroxy alkyl, haloalkyl, aminoalkyl, mono- and di-alkylamino alkyl, amino, alkylamino, or dialkylamino;

$R_4$ is H, alkyl, or acyl;

$R_5$ is H or alkyl;

$R_6$ is H, alkyl or acyl;

and wherein:

a is 0 or 1;
b is 1 or 2;
c is 0, 1 or 2;
d is 0, 1, 2 or 3;
e is 1 or 2;
f is 1, 2, 3, or 4;

and the acid addition salts thereof.

Compounds within the scope of Formula I exhibit physiological activity in mammals including anti-secretory activity as histamine $H_2$-receptor antagonists and cytoprotective activity.

This invention also relates to methods for the treatment and prevention of gastrointestinal hyperacidity and ulcerogenic disorders in humans and other mammals comprising administering to a patient an effective amount of a compound with the description of Formula I.

DETAILED DESCRIPTION OF THE INVENTION

Preferred classes of compounds are described with respect to Formula I as follows:

(A) Wherein:
$W_1$, $W_2$ and $W_3$ are CH;
b and c are 1; and
$R_1$ together with $W_1$ forms a double bond;

or (B) Wherein:
$W_1$ is $CHR_3$ or $CH_2$; and
$W_2$ and $W_3$ are $CH_2$;

or (C) Wherein either A or B above apply, and
X is $(CH)_{3-d}$;
Y is $(CH)_d$;
Z is O; and
a is zero;

or (D) Wherein either A or B above apply, and
X is N or CH;
Y is O, S or $NR_4$;
Z is S; and
a is 1.

A most preferred class of compounds within the scope of Formula I comprises the isoquinoline and the di- and tetrahydroisoquinoline compounds. Of this class, the compounds of Formulae II and III are of particular interest.

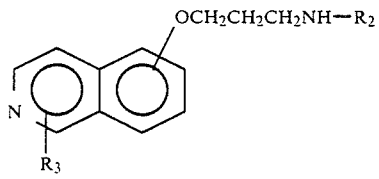

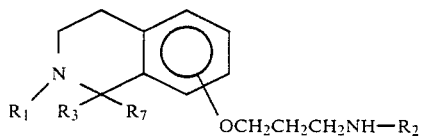

In Formulae II and III, $R_2$ and $R_3$ are as defined above; $R_1$ is H, alkyl, substituted alkyl, acyl or together with $R_7$ forms a carbon-nitrogen double bond; and $R_7$ is H or together with $R_1$ forms a carbon-nitrogen double bond; provided that in Formula III when $R_1$ and $R_7$ form a double bond then $R_3$ is amino, alkylamino or dialkylamino. In Formulae II and III, the $NHR_2$ propoxy substituent may be substituted at the 5, 6, 7 or 8 position.

Another preferred embodiment of this invention comprises the bicyclic compounds including a heteroatom in both rings and including a thioether ring substituent as defined herein. This embodiment includes the compounds of Formulae IV and V

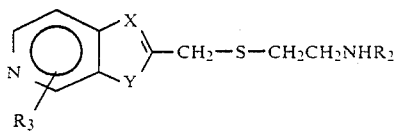

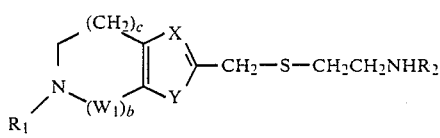

wherein $W_1$ is $CR_3R_7$ when b is 1 or $CH_2$ when b is 2, and $R_1$, $R_2$, $R_3$, $R_7$, X, Y, b and c are as defined above.

A particularly interesting class of compounds according to Formula V comprises those compounds wherein Y is oxygen and b and c are 1.

The compounds of Formulae I to V may also form hydrates and exhibit tautomerism. Formula I is intended to encompass all hydrates and tautomers, as well as any diastereomers and optical enantiomers.

As employed above and throughout the disclosure, the following terms, unless otherwise indicated, shall be understood to have the following meanings:

"Alkyl" means a saturated aliphatic hydrocarbon which may be either straight- or branched-chained. Preferred alkyl groups have no more than about 6 carbon atoms and may be methyl, ethyl and structural isomers of propyl, butyl, pentyl, and hexyl.

"Lower alkyl" means an alkyl group as above, having 1 to about 4 carbon atoms. Examples of lower alkyl groups are methyl, ethyl, n-propyl, isopropyl, butyl, sec-butyl, and tert-butyl.

The term "halo" includes all four halogens; namely, fluorine, chlorine, bromine and iodine. Fluorine and chlorine are preferred.

The "acyl" radical may be any organic radical derived from an organic acid by the removal of its hydroxyl group such as acetyl, propionyl, 3-carboxy propionyl, benzoyl, etc. Preferred acyl radicals are radicals of lower alkyl organic acids.

"Substituted alkyl" means an alkyl group substituted by a halo, alkoxy, hydroxy, amino, mono- or di-alkylamino group.

"Haloalkyl" means an alkyl group substituted by a halo group. The haloalkyls include groups having one or more halo substituents which may be the same or different, such as trifluoromethyl.

"Alkoxy" means the oxy radical of an alkyl group, preferably a lower alkyl group, such as methoxy, ethoxy, n-propoxy, and i-propoxy.

"Alkoxy alkyl" means an alkyl group substituted by an alkoxy group as defined above.

"Hydroxy alkyl" means an alkyl group substituted by a hydroxy group.

"Amino alkyl" means an alkyl group substituted by an amino group.

"Mono- or di-alkylamino alkyl" means an alkyl group substituted by an alkyl- or di-alkyl-substituted amino group.

"Alkylamino" means a primary or secondary alkyl-substituted amino group.

Representative examples of compounds of this invention are listed below in Tables A, B, C and D.

TABLE A

Structure: isoquinoline with OCH₂CH₂CH₂NHR₂ substituent and R₃ at position 1 wherein substitution may be at the 5,6,7 or 8 position

| R₂ | R₃ |
|---|---|
| -C(=NHCN)-NHCH₃ | H |
| -C(=NCN)-NH₂ | CH₃ |
| -C(=CHNO₂)-NHCH₃ | H |
| -C(=CHNO₂)-NH₂ | NH₂ |
| -C(=N-CN)-S-CH₃ | H |
| -C(=N-CN)-S-CH₃ | CH₃ |
| -C(=N-CN)-S-CH₃ | NH₂ |
| -C(=N-CN)-S-CH₃ | N(CH₃)₂ |
| (piperazinone with CH₂-benzodioxole substituent, =N-) | NHCH₃ |
| (piperazinone with CH₂-(6-methylpyridin-3-yl) substituent, =N-) | H |
| 4-amino-3-methyl-1,2,5-thiadiazole 1-oxide | CH₃ |
| 4-methylamino-3-methyl-1,2,5-thiadiazole 1-oxide | H |

TABLE A-continued wherein substitution may be at the 5,6,7 or 8 position

| R₂ | R₃ |
|---|---|
| 1-methyl-3-(propan-2-ylidene)-5-amino-1,2,4-triazole | NH₂ |
| 1-ethyl-3-(propan-2-ylidene)-5-methylamino-1,2,4-triazole | H |
| 1H-3-(propan-2-ylidene)-5-methylamino-1,2,4-triazole | H |

TABLE B

Structure: tetrahydroisoquinoline with OCH₂CH₂CH₂NHR₂ substituent, N-R₁, and R₃, R₇ at position 1 wherein substitution may be at the 5,6,7 or 8 position

| R₁ | R₂ | R₃ | R₇ |
|---|---|---|---|
| CH₃ | -C(=NCN)-NHCH₃ | H | H |
| CH₃ | -C(=CHNO₂)-NHCH₃ | CH₃ | H |
| CH₃ | 1,3-dimethyl-5-amino-1,2,4-triazol-3-ylidene | NHCH₃ | H |
| double bond with R₇ | (piperazinone with CH₂-benzodioxole substituent) | CH₃ | double bond with R₁ |
| double bond with R₇ | (piperazinone with CH₂-(6-methylpyridin-3-yl) substituent) | NHCH₃ | double bond with R₁ |
| double bond with R₇ | 4-amino-3-methyl-1,2,5-thiadiazole 1-oxide | N(Et)₂ | double bond with R₁ |

TABLE B-continued

Structure: 1,2,3,4-tetrahydroisoquinoline with -OCH₂CH₂CH₂NHR₂ substituent on the benzene ring, N-R₁, with R₃ and R₇ on the carbon adjacent to N.

wherein substitution may be at the 5, 6, 7 or 8 position

| R₁ | R₂ | R₃ | R₇ |
|---|---|---|---|
| double bond with R₇ | 4-amino-3-methyl-1,2,5-thiadiazole 1,1-dioxide (=C(NH₂)-C(CH₃)=N-S(O₂)-N=) | NH₂ | double bond with R₁ |
| CH₃ | 4-amino-3-methyl-1,2,5-thiadiazole 1,1-dioxide | H | H |
| CH₃ | 4-(methylamino)-3-methyl-1,2,5-thiadiazole 1-oxide | H | H |
| CH₃ | 2-[(5-methyl-2-pyridinyl)methyl]-3-imino-propanamide type (HN-C(=O)-C(=CH-N=)-CH₂-(6-methylpyridin-3-yl)) | H | H |
| Et | analogous with 1,3-benzodioxol-5-yl instead of methylpyridinyl | H | H |
| Et | 1-methyl-3-(methylamino)-1,2,4-triazole derivative (CH₃-N-N=C(-N=)-NHCH₃ with =C(CH₃)-) | H | H |
| Et | -C(=CHNO₂)-NH₂ | H | H |
| CH₃ | -C(=NCN)-SCH₃ | CH₃ | H |
| n-propyl | -C(=N-CN)-NHCH₃ | H | H |

TABLE C

Structure: furo[or thieno]pyridine with -CH₂SCH₂CH₂NHR₂ substituent, Y in ring, R₃ on pyridine.

Y may be oxygen or sulfur

| R₂ | R₃ |
|---|---|
| -C(=NHCN)-NHCH₃ | H |
| -C(=NCN)-NH₂ | CH₃ |
| -C(=CHNO₂)-NHCH₃ | H |
| -C(=CHNO₂)-NH₂ | NH₂ |
| -C(=N-CN)-S-CH₃ | H |
| HN-C(=O)-C(=CH-N=)-CH₂-(1,3-benzodioxol-5-yl) | NHCH₃ |
| HN-C(=O)-C(=CH-N=)-CH₂-(6-methylpyridin-3-yl) | H |
| 4-amino-3-methyl-1,2,5-thiadiazole 1-oxide | CH₃ |
| 4-(methylamino)-3-methyl-1,2,5-thiadiazole 1-oxide | H |
| 1-methyl-3-amino-5-methyl-1,2,4-triazol-5-amine derivative | NH₂ |
| 1-ethyl-3-(methylamino)-5-methyl-1,2,4-triazole derivative | H |

TABLE C-continued

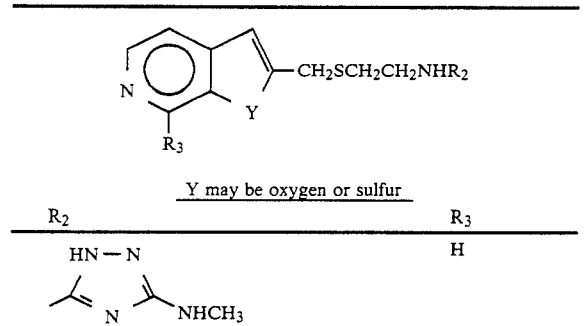

Y may be oxygen or sulfur

| $R_2$ | $R_3$ |
|---|---|
| ![HN-N / =N / NHCH3 group] | H |

TABLE D

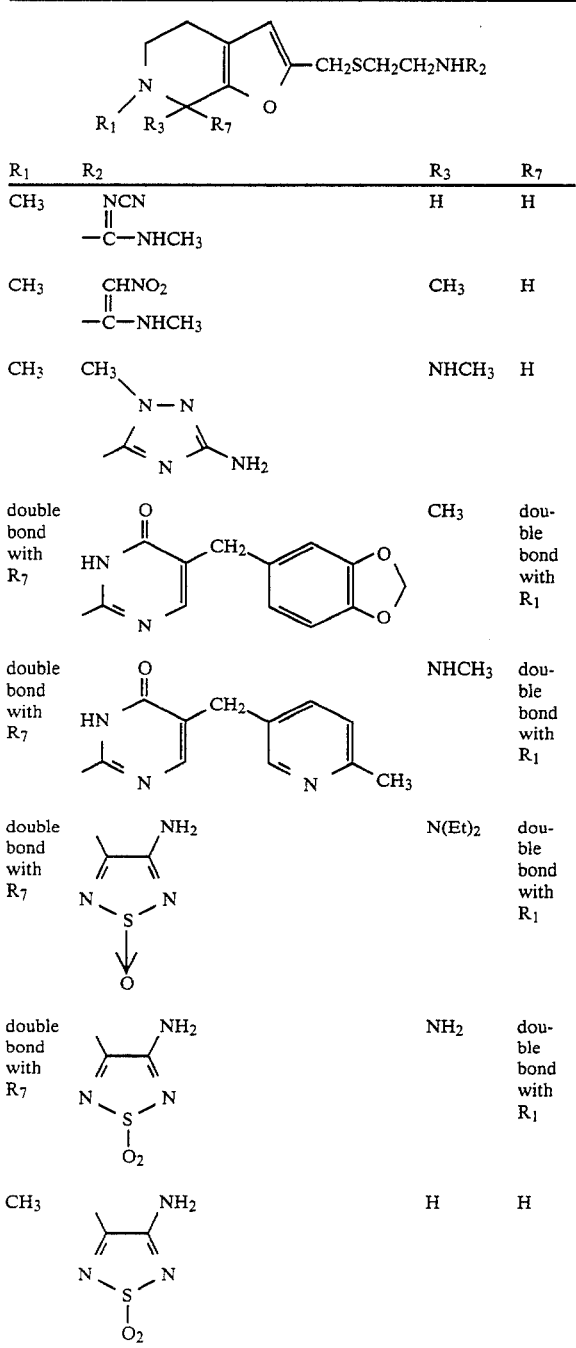

| $R_1$ | $R_2$ | $R_3$ | $R_7$ |
|---|---|---|---|
| $CH_3$ | $\underset{\overset{\|}{-C-NHCH_3}}{NCN}$ | H | H |
| $CH_3$ | $\underset{\overset{\|}{-C-NHCH_3}}{CHNO_2}$ | $CH_3$ | H |
| $CH_3$ | $CH_3$-N-N / =N / NH_2 | $NHCH_3$ | H |
| double bond with $R_7$ | (HN-C(=O)-C(=CH-N=)-CH_2-benzodioxole) | $CH_3$ | double bond with $R_1$ |
| double bond with $R_7$ | (HN-C(=O)-C(=CH-N=)-CH_2-pyridine-CH_3) | $NHCH_3$ | double bond with $R_1$ |
| double bond with $R_7$ | (thiadiazole-S-oxide with NH_2) | $N(Et)_2$ | double bond with $R_1$ |
| double bond with $R_7$ | (thiadiazole-S-dioxide with NH_2) | $NH_2$ | double bond with $R_1$ |
| $CH_3$ | (thiadiazole-S-dioxide with NH_2) | H | H |

TABLE D-continued

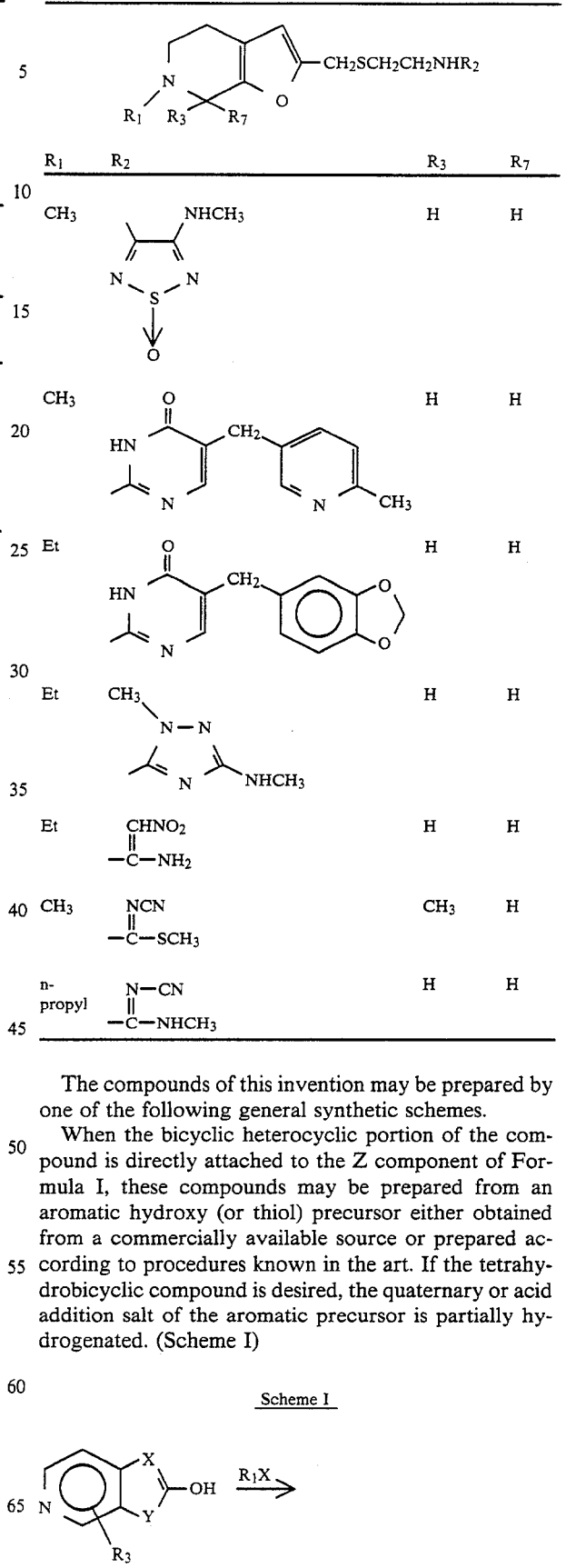

| $R_1$ | $R_2$ | $R_3$ | $R_7$ |
|---|---|---|---|
| $CH_3$ | (thiadiazole-S-oxide with NHCH_3) | H | H |
| $CH_3$ | (HN-C(=O)-C(=CH-N=)-CH_2-pyridine-CH_3) | H | H |
| Et | (HN-C(=O)-C(=CH-N=)-CH_2-benzodioxole) | H | H |
| Et | $CH_3$-N-N / =N / NHCH_3 | H | H |
| Et | $\underset{\overset{\|}{-C-NH_2}}{CHNO_2}$ | H | H |
| $CH_3$ | $\underset{\overset{\|}{-C-SCH_3}}{NCN}$ | $CH_3$ | H |
| n-propyl | $\underset{\overset{\|}{-C-NHCH_3}}{N-CN}$ | H | H |

The compounds of this invention may be prepared by one of the following general synthetic schemes.

When the bicyclic heterocyclic portion of the compound is directly attached to the Z component of Formula I, these compounds may be prepared from an aromatic hydroxy (or thiol) precursor either obtained from a commercially available source or prepared according to procedures known in the art. If the tetrahydrobicyclic compound is desired, the quaternary or acid addition salt of the aromatic precursor is partially hydrogenated. (Scheme I)

Scheme I

-continued
Scheme I

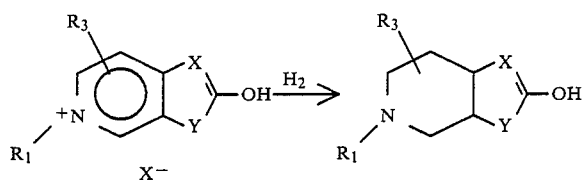

When R₃ is other than hydrogen, for example when an amino group is present in the 1-position, the dihydrocompound may be prepared by an electrophilic cyclization of a 2-(N-formyl)ethyl aromatic compound. (Scheme II)

Scheme II

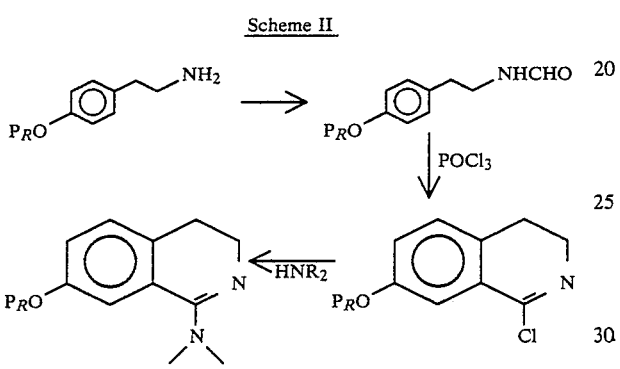

The protecting group, $P_R$, may be methyl, benzyl or the N-phthalimido propyl bromide as described above. If the protecting group is chosen to be other than the N-phthalimido propyl bromide, the protecting group is removed according to methods known in the art, and the formation of the ether linkage is accomplished by treating the hydroxy compound with a protected N-propylbromide in the presence of strong base such as sodium methoxide. Ether coupling reagents other than a base and a bromide may also be used. (Scheme III)

Scheme III

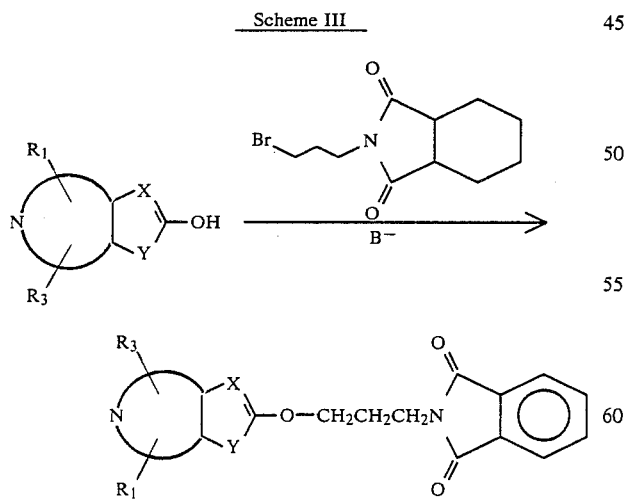

The nitrogen protecting group is preferably phthalimido but can be any protecting group insensitive to the ether formation reaction conditions, such as a base insensitive group.

The amine compound is obtained by the removal of the protecting group, for example, the phthalimido group is removed with hydrazine hydrate. (Scheme IV)

Scheme IV

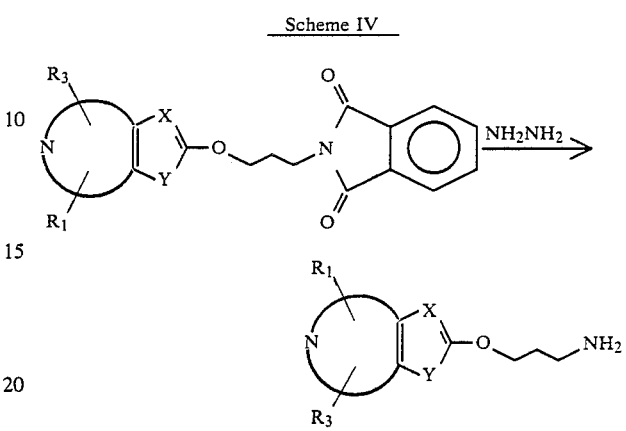

In the case where R₂ is other than hydrogen, the addition of the terminal R₂ group comprises treating the amine with an R₂ end group precursor unit including those groups listed in Scheme V. The preparation of the precursors of the R₂ groups and the reaction conditions under which they are coupled to the primary amine are fully described in U.S. Pat. Nos. 4,104,381, 4,279,819, 4,323,566 and GB 2067987A, hereby incorporated by reference.

Scheme V

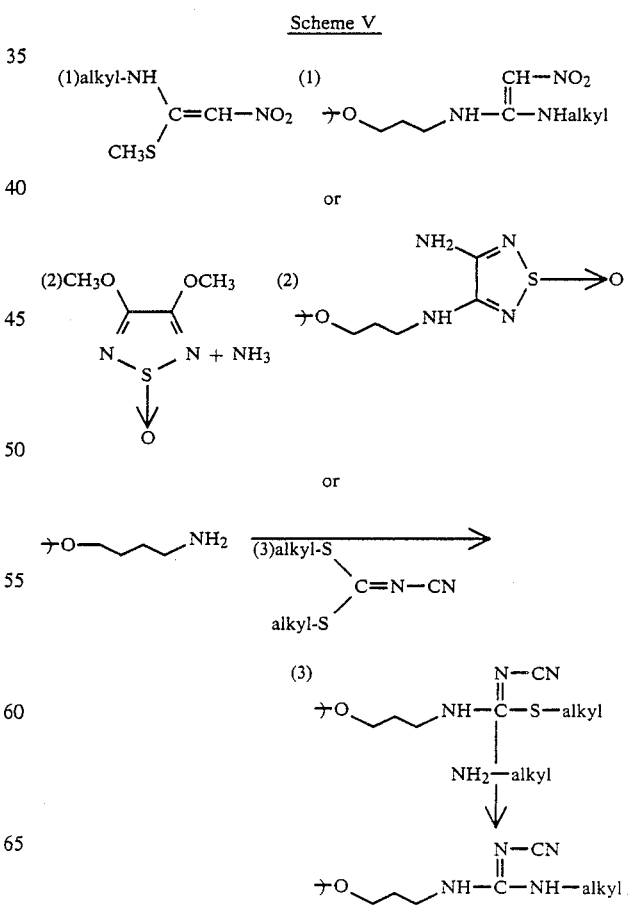

Treatment of the S-alkyl compound with a primary amine results in the N-cyano, N-methyl guanidine analog compound.

Compounds within the scope of Formula I and having a methyleneoxy or methylenethioxy substituent (a=1) on the bicyclic portion of the compound may be prepared by one of the reaction sequences described below.

The methyleneoxy or methylenethioxy ether may be prepared from the coupling of a 2-thioethylamine with the methylene hydroxy ring system according to Scheme VI.

Scheme VI

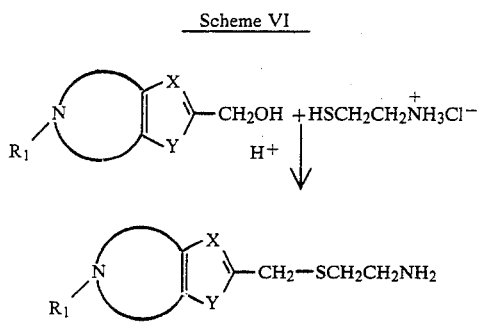

Addition of the $R_2$ group may proceed as described above in Scheme V.

The furano or thienyl bicyclic systems may be prepared by one of many pathways including reaction sequences which build the furan or thiophene ring about the preformed nitrogen-containing ring or which start with the furan or thiophene rings. Exemplary synthetic pathways are described below in Schemes VII to IX.

Scheme VII

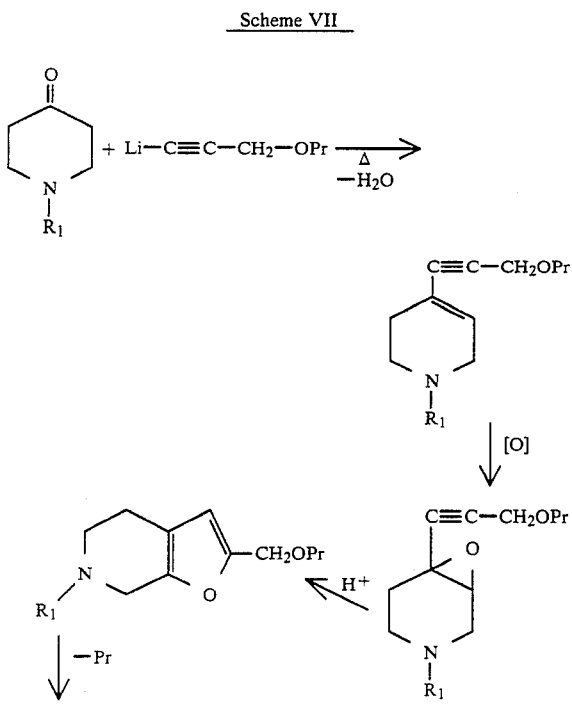

-continued
Scheme VII

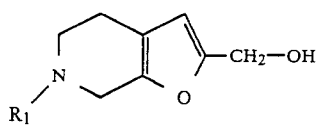

Scheme VII starts with a preformed nitrogen-containing ring ketone which is either commercially available or prepared by procedures known in the literature. The ketone is reacted with an acetylenic nucleophile having a protected alcohol group in a solvent system below room temperature. The alcoholic addition product is readily dehydrated to form the conjugated triple double bond system by treatment with mild acid. Selective oxidation of the double bond with a peroxide forms the epoxide which under acidic conditions rearranges to form the furan moiety. The alcohol is then deprotected. Compounds having symmetrical substituents in the 5- and 7-positions of the bicyclic ring (counting the furano oxygen as the 1-position and the pyridinyl nitrogen as the 6-position) may be prepared by this route.

Aromatic bicyclics may be prepared by cyclizing an appropriately substituted 3-hydroxy-4-(3'-hydroxy-1-propynyl)-pyridine prepared according to Scheme VIII.

Scheme VIII

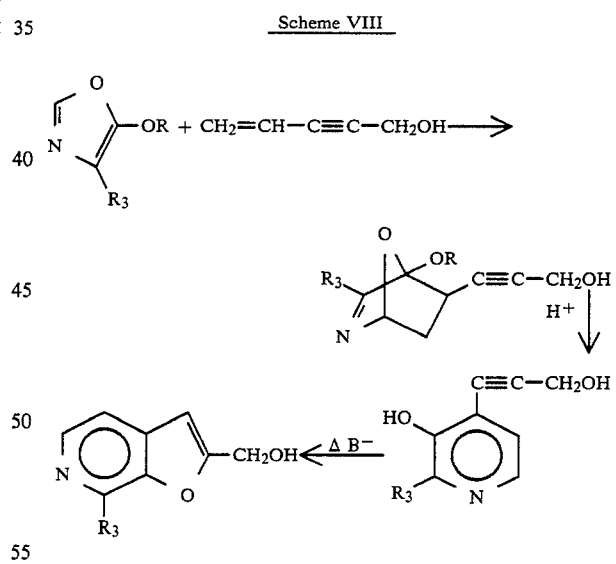

Treatment of a 5-alkoxy oxazole with a vinyl hydroxymethyl acetylene (the hydroxy group may or may not be protected) at elevated temperature and/or pressure results in the oxy bridged ring Diels-Alder product. Treatment of the bridged ring system with mild acid forms the 3-hydroxy, 4-oxymethylacetylenic pyridine which upon treatment with base forms the 2-oxymethyl-furano[2,3-c]pyridine.

Another route to this ring system proceeds by way of the 2-methyl furan as the starting point, as shown in Scheme IX.

Scheme IX

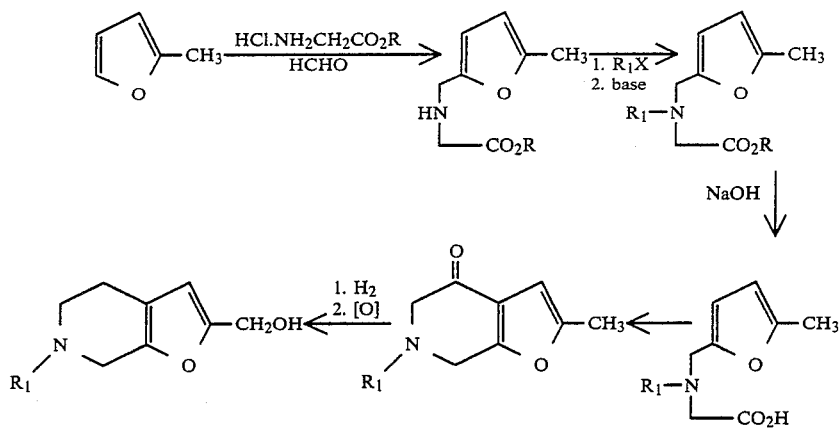

Exemplary reaction conditions for the synthetic sequence of Scheme IX are described by Mertes, *J. Org. Chem*, 33, 133 (1968). The keto function is removed by reduction, hydrogenation or the like to obtain the tetrahydro compound. The hydroxy methyl group then is introduced by the oxidation of the 2-methyl group by methods known in the art.

The compounds of this invention may be readily converted to their non-toxic acid addition salts by customary methods in the art. The non-toxic salts of this invention are those salts the acid component of which is pharmacologically acceptable in the intended dosages, including those prepared from inorganic acids such as hydrochloric acid, hydrobromic acid, sulfuric acid, nitric acid and phosphoric acid, and from organic acids such as methane sulfonic acid, benzenesulfonic acid, acetic acid, propionic acid, malic acid, oxalic acid, succinic acid, glycolic acid, lactic acid, salicylic acid, benzoic acid, nicotinic acid, phthalic acid, stearic acid, oleic acid, abietic acid, etc.

The following are selected examples of the preparation of the compounds according to this invention.

EXAMPLE 1

PREPARATION OF 1-CYANO-3-[3-(5-ISOQUINOLYLOXY)ISO-PROPYL]-2-METHYL-PSEUDOTHIOUREA

Step 1

5-(3-Phthalimido)propoxy isoquinoline 5-hydroxyisoquinoline (39.3 g) is dissolved in dimethylformamide (350 ml). The solution is purged with nitrogen for several minutes. Anhydrous potassium carbonate (41.2 g) and N-(3-bromopropyl)phthalimide (72.7 g) are added to the solution and the reaction mixture is stirred for four days at RT under $N_2$. The mixture is poured into 1 liter of $H_2O$, stirred for 1½ hours and filtered. The resulting solid is washed with $H_2O$ and partially dried in air. The wet solid is added to $CHCl_3$ (1¼ liters) and the mixture is slowly filtered and rinsed with $CHCl_3$ (500 ml). The layers are separated, the chloroform layer dried over $Na_2SO_4$, filtered and the filtrate evaporated in vacuo to yield the phthalimido isoquinoline as a dark purple solid.

Step 2

5-(3-Aminopropoxy)isoquinoline

The dark purple solid of Step 1 is added to 750 ml of absolute ethanol. 17 ml of an 85% solution of hydrazine hydrate are added to the solution. The reaction mixture is stirred under reflux for 3 hours, filtered and the dark red filtrate evaporated in vacuo. The residue is dissolved in 750 ml of concentrated HCl, stirred for 1 hour and filtered, and the filtered solid rinsed with a 5% HCl solution. The dark filtrate is alkalinized with a 50% aqueous NaOH solution and stirred with 500 ml methylene chloride. The layers are separated and the aqueous layer extracted with methylene chloride. The methylene chloride extract is washed with saturated NaCl solution and dried over $Na_2SO_4$. The dried extract is filtered and the filtrate evaporated in vacuo yielding a dark red oil. The oil is distilled under vacuum and the distillate fractionating up to a temperature of approximately 205° C. at 1 mm Hg is collected. The distillate is a mixture of the aminopropoxyisoquinoline as a viscous yellow oil and a smaller amount of a gel. The major portion of the oil is decanted from the gel and dissolved in methanol. Methanesulfonic acid (98% solution) is added to the methanol solution and the mixture evaporated in vacuo. The residue is dissolved in absolute ethanol causing the precipitation of crystals. The precipitate is filtered, and the solid washed with ethanol, diethyl ether and dried under house vacuum at approximately 70° C. for 2 hrs, yielding the methanesulfonic acid salt of the aminopropoxyisoquinoline as a very light green powder, M.P. 180°–182° C.

Step 3

1-Cyano-3-[3-(5-isoquinolyloxy)isopropyl]-2-methyl-pseudothiourea 8 g of the aminopropoxy isoquiniline of Step 2 in 10 ml of isopropanol is added to a solution of 5.78 g of S,S-dimethyl-N-cyaniminodithiocarbonimidate dissolved in isopropanol. A white precipitate forms immediately and the reaction mixture is stirred overnight at RT under nitrogen. The mixture is slowly filtered and the solid washed with isopropanol and diethyl ether and then dried in air yielding the pseudothiourea as a white solid, M.P. 164°–165° C.

The Methanesulfonic Salt of 1-Cyano-3-[3-(5-isoquinolyloxy)isopropyl]2-methyl-pseudothiourea 1.13 ml of a solution of methanesulfonic acid (98%) are added to a solution of 3.4 g of the pseudothiourea dissolved in 100 ml of methanol. The resulting solution is evaporated in vacuo. The solid residue is triturated in 40 ml absolute ethanol, the resulting solution filtered, the solid washed with ethanol and diethyl ether, dried in air, stored in a vaccuum dessicator overnight, and dried under house vacuum for 2 hrs, yielding the methanesulfonic acid salt as a very light green powder, M.P. 186°–188° C.

EXAMPLE 2

THE PREPARATION OF 2-CYANO-1-[3-(5-ISOQUINOLYLOXY)PROPYL]-3-METHYL GUANIDINE HYDROCHLORIDE

A solution of 14.3 g anhydrous methylamine in 75 ml absolute ethanol is added to a solution of 7.0 g of the pseudothiourea compound obtained in Step 3 dissolved in 100 ml methanol. The reaction mixture is stirred with nitrogen purge overnight. While cooling in an ice bath, approximately 22 g methylamine is bubbled into the reaction mixture. The reaction mixture is allowed to warm to RT while stirring is continued and then heated to reflux for 1 hr. After cooling, the solution is filtered and the resulting solid washed with ethanol, diethyl ether and dried in air, yielding the desired guanidine as a white solid. The solid is suspended in methanol and the pH adjusted to 3-4 with methanolic HCl. This solution is filtered and the filtrate evaporated in vacuo. The residue is triturated in ethyl acetate, filtered and the solid washed with ethyl acetate and diethyl ether. The solid is dried and stored in a vacuum dessicator, yielding the hydrochloride salt of the desired guanidine as a light powder, M.P. 177°–179° C.

EXAMPLE 3

THE PREPARATION OF N-METHYL-N'-[3-[5-(2-METHYL-1,2,3,4-TETRAHYDROISOQUINOLYLOXY)]PROPYL]-2-NITRO-1,1-DIAMINOETHENE

Step 1

5-Hydroxy-2-methyl-isoquinolenium iodide 24.7 g of 5-hydroxyquinoline (technical grade) is dissolved in boiling absolute ethanol (350 ml). The resulting solution is filtered and washed with hot ethanol. Iodomethane (50 g) is added to the solution, which is stirred under reflux for 2½ hours. The mixture is cooled, filtered and the precipitate washed with absolute ethanol, anhydrous diethyl ether, and dried in air, yielding the isoquinolenium iodide as a light brown, fluffy solid, M.P. 236°–237° C.

Step 2

5-Hydroxy-2-methyl-1,2,3,4-tetrahydroisoquinoline

The isoquinolenium methiodide of Step 1 (31 g) is dissolved in 650 ml of a 10% water in methanol (w/v) solution. Sodium borohydride (17.2 g) is added to the solution under a blanket of nitrogen, over a period of 15 minutes, while the mixture is heated to boiling. After completing the addition, the mixture is refluxed for ten minutes. Acetone (250 ml) is added and the resulting mixture allowed to cool and evaporated in vacuo. The residue is shaken with 375 ml of a 3.5% sodium carbonate solution. The resulting slurry is filtered, the solid washed with 200 ml water and dried on a Buchner overnight, yielding the tetrahydroisoquinoline as a light beige powder, M.P. 183.5° C.

Step 3

2-Methyl-5-[3-(N-phthalimido)-propoxy]-1,2,3,4-tetrahydroisoquinoline 41.5 g of the tetrahydroisoquinoline are mixed with 500 ml of methanol, 13.7 g sodium methoxide added to the stirred mixture and the solution evaporated in vacuo. The residue is dissolved in dimethylformamide, 68.1 g of N-(3-bromopropyl)phthalimide added and the mixture stirred at RT for 20 hours. The reaction mixture is partitioned between water and ethyl acetate. The layers are separated and the aqueous layer extracted with ethyl acetate. The combined organic extract is washed with water, saturated sodium chloride, dried over sodium sulfate, filtered, and the filtrate evaporated in vacuo yielding a light brown solid. The solid is dissolved in hot absolute ethanol, the solution filtered, the solid rinsed with hot ethanol and the filtrate cooled at RT and in an ice bath. The resulting mixture is filtered, the solid washed with cold ethanol and dried in air, yielding the phthalimido product as a white solid, M.P. 111°–112° C.

Step 4

2-Methyl-5-(3-aminopropoxy)-1,2,3,4-tetrahydroisoquinoline 34.2 g of the phthalimido compound is mixed in 350 ml of absolute ethanol. 6.9 ml of a 85% hydrazine hydrate solution is added and the mixture heated to reflux for three hours. The mixture is cooled, filtered and the filtrate evaporated in vacuo. The residue is triturated with a 5% HCl solution and the slurry is slowly filtered. The clear filtrate is alkalinized by adding a 50% NaOH solution. The resulting oily precipitate is extracted with diethyl ether, washed with saturated NaCl, dried over $Na_2SO_4$, filtered and evaporated in vacuo yielding the aminopropoxy compound as a light yellow oil, which crystallizes on standing.

Step 5

N-Methyl-N'-[3-[5-(2-methyl-1,2,3,4-tetrahydroisoquinolyloxy)]propyl]-2-nitro-1,1-diaminoethene 5.47 g of the aminopropoxy compound of Step 4 and 3.68 g of 1-nitro-2-methylamino-2-methylthioethene are mixed in 50 ml of absolute ethanol and heated to reflux with stirring for an hour and 15 minutes. The reaction mixture is cooled and evaporated in vacuo. The residue is triturated with hot ethyl acetate, stirred in ethyl acetate and filtered. The filtered solid is washed with ethyl acetate and dried, yielding the diamino ethene as a white powder, M.P. 133°–135° C., which is recrystallized from acetone, M.P. 136.8° C.

EXAMPLE 4

THE PREPARATION OF 2-CYANO-1-METHYL-3-[3-[5-(2-METHYL-1,2,3,4-TETRAHYDROISOQUINOLYLOXY)]PROPYL]-GUANIDINE

Step 1

1-Cyano-2-methyl-3-[3-[5-(2-methyl-1,2,3,4-tetrahydroisoquinolyloxy)]propyl]pseudothiourea 60 g of S,S-dimethyl-N-cyanoiminodithiocarbonimidate is dissolved in 75 ml isopropanol and the mixture stirred at RT while purging with $N_2$. 9.0 g of methylamine in 20 ml isopropanol is added to the mixture and stirring is continued overnight. Isopropanol is added to the solidified mixture and the thick slurry filtered, washed with isopropanol, diethyl ether and air-dried, yielding the pseudothiourea as a white solid, M.P. 135.6° C.

The pseudothiourea is dissolved in methanol, acidified with methanol/HCl and evaporated to dryness. The solid is triturated in absolute ethanol, stirred in ethanol and filtered. The resulting solid is washed with ethanol, diethyl ether, dried in air and under house vacuum, yielding the hydrochloride salt as a white solid, M.P. 170°–172° C.

Step 2

2-Cyano-1-methyl-3-[3-[5-(2-methyl-1,2,3,4-tetrahydroisoquinolyloxy)]propyl]guanidine 6.0 g of the S-methyl compound is dissolved in 120 ml of warm absolute ethanol. 12.2 g of anhydrous methylamine in 50 ml absolute ethanol are added to the cooled ethanolic solution and stirred at RT overnight. The reaction mixture is filtered and the solid washed with ethanol, diethyl ether and dried in air, yielding the desired guanidine as a white powder, M.P. 90°–96° C.

This powder is suspended in 50 ml methanol and slightly acidified with methanol/HCl. The solution is filtered and the filtrate evaporated in vacuo resulting in a clear oil and foam which is dissolved in absolute ethanol and recrystallized twice yielding the hydrochloride guanidine salt, M.P. 170°–172° C.

EXAMPLE 5

THE PREPARATION OF 2-CYANO-1-[3-(7-ISOQUINOLYLOXY)PROPYL]-3-METHYL GUANIDINE

Step 1

(N-phthalimido)-7-(3-propoxy)isoquinoline

Sodium methoxide (11.6 g) is added to a mixture of 2-hydroxyisoquinoline (31.1 g) in 400 ml methanol. The reaction mixture is evaporated in vacuo and the residue dissolved in dimethylformamide. N-(3-bromo-propyl)-phthalimide (57.6 g) is added to the solution and stirred overnight at RT. The reaction mixture is poured into H₂O, creating a yellow precipitate. The suspension is stirred for 1 hour, filtered, the solid washed with H₂O. The moist solid is stirred in absolute ethanol for 1 hour, filtered and washed with ethanol/H₂O (1:1) and dried in air. The phthalimido compound is obtained by recrystallizing the yellow solid from boiling absolute ethanol.

Step 2

7-(3-aminopropoxy)isoquinoline

Hydrazine hydrate (8 ml of an 85% solution) is added to a stirred suspension of the phthalimido compound of Step 1 (37.4 g) in absolute ethanol and the reaction mixture is heated to reflux for 3 hours, cooled and filtered. The resulting solid is washed with ethanol and the filtrate evaporated in vacuo. The evaporated residue is triturated in 250 ml of a 5% HCl solution, slowly filtered and the filtrate stored in the refrigerator overnight. The next day the solution is washed with methylene chloride and alkalinized with a 50% aqueous sodium hydroxide solution, giving an oily precipitate. The aqueous layer is extracted with methylene chloride and the combined organic extracts washed with saturated sodium chloride solution and dried over sodium sulfate. After filtering the resulting mixture, the filtrate is evaporated in vacuo to give the aminopropoxy compound as an amber oil. The dihydrochloride acid salt of the aminopropoxy compound is prepared by the addition of a methanolic HCl solution to a methanol solution of the amber oil, and after drying the salt under vacuum, yields a light yellow powder, M.P. 212°–215° C.; the methanesulfonic acid salt is a white powder, M.P. 182°–183° C.

Step 3

3-[3-(8-Isoquinolyloxy)propyl]-2-methylpseudothiourea 11.0 g of 7-(3-aminopropoxy)isoquinoline in 20 ml isopropanol is added to a solution of S,S-dimethyl-N-cyanoiminodithiocarbonimidate (7.2 g) in 90 ml isopropanol. The reaction mixture is stirred at RT for 2 hours. The mixture is filtered, the resulting solid washed with isopropanol, diethyl ether, and dried in air, yielding the desired pseudothiourea as a white powder, M.P. 112°–114° C. The methanesulfonic acid salt of the pseudothiourea crystallizes from methanol as a light yellow solid, M.P. 202°–204° C.

Step 4

2-Cyano-1-[3-(7-isoquinolyloxy)propyl]-3-methylguanidine

A solution of anhydrous methylamine (18.2 g) in 90 ml of absolute ethanol is added to a stirred suspension of the pseudothiourea (8.4 g) obtained in Step 3 in 175 ml methanol. The reaction mixture is stirred at RT overnight, filtered, the resulting solid washed with ethanol and diethyl ether, and dried in air, yielding the desired isoquinolyloxy guanidine as a white fluffy powder, M.P. 175°–177° C. The methanesulfonic acid salt of the guanidine is recrystallized twice from ethanol and methanol to give a near-white powder, M.P. 162.5°–164° C.

EXAMPLE 6

THE PREPARATION OF 2-CYANO-1-METHYL-3-[3-[7-(2-METHYL-1,2,3,4-TETRAHYDROISOQUINOLYLOXY)]PROPYL GUANIDINE

Step 1

7-Hydroxy-2-methylisoquinolenium iodide 153 g of iodomethane is added to a suspension of 7-hydroxyisoquinoline (78.2 g) in 1 liter absolute ethanol. The mixture is stirred at reflux for two hours, cooled, and filtered. The solid is washed with ethanol and diethyl ether and dried in air, yielding the methyliodide salt of the isoquinoline as brown crystals, M.P. 233°–235° C.

Step 2

7-Hydroxy-2-methyl-1,2,3,4-tetrahydroisoquinoline 41.6 g of NaBH₄ are slowly added over a period of 30 minutes to a stirred solution of the methiodide of Step 1 (75.0 g) in 1550 ml of 10% H₂O in methanol under a stream of nitrogen. After the addition is complete, the mixture is kept at reflux for 20 minutes, after which 700 ml acetone are added, and the mixture is cooled and evaporated in vacuo. The residue is shaken with a 3.5% sodium carbonate solution, filtered and the solid washed with H₂O and dried in air overnight, giving the desired tetrahydroisoquinoline as a fluffy, near-white powder, M.P. 167°–169° C.

Step 3

2-Methyl-7-[3-(N-phthalimido)propoxy]-1,2,3,4-tetrahydroisoquinoline 10.1 g of sodium methoxide is added to a solution of the tetrahydroisoquinoline of Step 2 (30.7 g) in methanol and the resulting mixture evaporated in vacuo. The oily residue is dissolved in dimethylformamide and 50.4 g of N-(3-bromopropyl)phthalimide added to the solution. The reaction mixture is stirred at RT for 21 hours and partitioned between H₂O and ethyl acetate. The layers are separated and the aqueous layer extracted with ethyl acetate. The combined organic extract is washed with H₂O and saturated NaCl solution, dried over sodium sulfate, filtered, and the filtrate evaporated in vacuo to give the desired product as a near-white solid.

Step 4

7-(3-Aminopropoxy)-2-methyl-1,2,3,4-tetrahydroisoquinoline 6.6 ml of an 85% hydrazine hydrate solution are added to a stirred suspension of the phthalimido isoquinoline of Step 3 (34.4 g) in 350 ml absolute ethanol. The reaction mixture is heated to reflux for 3 hours, allowed to cool and evaporated in vacuo. The residue is triturated with 250 ml 5% HCl and filtered. The clear filtrate is stored in the refrigerator overnight, extracted with methylene chloride, alkalinized with 50% sodium hydroxide solution, and extracted again with methylene chloride. The combined organic extract is washed with saturated NaCl solution, dried over sodium sulfate, filtered, and the filtrate evaporated in vacuo, giving the desired aminopropoxy compound as a light amber oil.

The monohydrate of the hydrochloride acid salt of the tetrahydroquinoline compound is a white solid, M.P. 120°–123° C.

Step 5

1-Cyano-2-methyl-5-[3-[8-(2-methyl-1,2,3,4-tetrahydroisoquinolyloxy)]propyl]pseudothiourea A suspension of the aminopropoxytetrahydroisoquinoline of Step 4 (7.1 g) in isopropanol is added to a solution of S,S-dimethyl-N-cyanoiminodithiocarbonimidate (4.7 g) in 60 ml isopropanol. The reaction mixture is stirred at RT for 1½ hours, filtered, the resulting solid washed with isopropanol and diethyl ether and dried in air, giving the desired pseudothiourea as a white powder, M.P. 147°–149° C.

Step 6

2-Cyano-1-methyl-3-[3-[7-(2-methyl-1,2,3,4-tetrahydroisoquinolyloxy)]propyl]guanidine A solution of anhydrous methylamine (9.8 g) in 50 ml absolute ethanol is added to a suspension of the pseudothiourea of Step 5 (4.5 g) in 50 ml methanol. The mixture is stirred overnight at RT and the resulting clear solution is evaporated in vacuo. The residue is dissolved in 75 ml hot isopropanol, filtered, cooled, and stirred for 2 hours. The suspension is filtered and the solid washed with isopropanol and diethyl ether and dried in air, giving the desired isoquinolyloxy guanidine as a white powder, M.P. 142°–144° C.

EXAMPLE 7

PREPARATION OF 3-AMINO-4-[3-[5-(2-METHYL-1,2,3,4-TETRAHYDROISOQUINOLYLOXY)]PROPYLAMINO]-1,2,5-THIADIAZOLE-1-OXIDE

A solution of 5.0 g of 5-(3-aminopropoxy)-2-methyl-1,2,3,4-tetrahydroisoquinoline in 50 ml of methanol is added, over a one-hour period, to a stirred solution of 3.68 g of 3,4-dimethoxy-1,2,5-thiadiazole-1-oxide in 200 ml methanol while maintaining the temperature at approximately 0° C. After stirring the mixture in an ice bath for 1½ hours, anhydrous ammonia (18.3 g) is bubbled in over a period of 10 minutes and stirring is continued at RT for 1½ hours. The reaction mixture is evaporated in vacuo and the residue (light foam/glass) is triturated in anhydrous ether. The resulting solid material is filtered, the solid washed with ether and dried in air, giving a white powder, melting with decomposition at 166°–171° C. The powder is dissolved in 10% methanol in methylene chloride, filtered and the impurities separated on a silica gel column. The purified fractions are evaporated in vacuo and the resulting foam triturated in ether, filtered, the solid washed with ether and dried in air, giving the desired thiadiazole-1-oxide as a white solid, M.P. 172°–174° C.

EXAMPLE 8

THE PREPARATION OF 3-AMINO-4-[3-[7-(2-METHYL-1,2,3,4-TETRAHYDROISOQUINOLYNOXY)]PROPYLAMINO]-1,2,5-THIADIAZOLE-1-OXIDE

A solution of 7-(3-aminopropoxy)-2-methyl-1,2,3,4-tetrahydroisoquinoline (5.43 g) in methanol (70 ml) is slowly added over a period of 45 minutes to a stirred solution of 3,4-dimethoxy-1,2,5-thiadiazole-1-oxide (3.68 g) in 375 ml of methanol at a temperature of 3° C. The reaction mixture is stirred for an additional one hour and 25.0 g anhydrous ammonia is bubbled in over a period of 10 minutes. The resulting mixture is warmed to RT with stirring and the solution is evaporated in vacuo. The near-white solid residue is dissolved in hot 95% ethanol, filtered hot and rinsed with hot ethanol. The solution is cooled with stirring, then stirred in an ice bath for 30 minutes and filtered. The resulting solid is washed with cold ethanol and diethyl ether and dried in air, giving the desired tetrahydroisoquinoline thiadiazole-1-oxide as a white powder, M.P. 193°–194° C.

The compounds of Formula I have been found to be histamine $H_2$-receptor antagonists by the results obtained in the following $H_2$-antagonist tests.

A. Isolated Guinea Pig Atria

The $H_2$-receptor antagonist activity of the compounds of Formula I is measured by observing the beat rate response versus compound concentration in isolated guinea pig atria. A discussion of criteria to evaluate these dose-response curves may be found in, E. J. Ariens, G. A. J. vanOs, A. M. Simonis, and T. M. van Rossum, "A Molecular Approach to General Pharmacology", Sections 11A, 11B, and 111, *Molecular Pharmacology: The Mode of Action of Biologically Active Compound.* Vol. 1, Academic Press (1964).

1. Tissue Bath

A fifty ml jacketed tissue bath is maintained at 30° C. The batch consists of a Krebs-Henseleit buffer aerated with 95% $O_2$–5% $CO_2$, (pH 7.4). The buffer is prepared by mixing: 4 ml of an aqueous (distilled deionized) solution of $CaCl_2.2H_2O$ (0.37 g/ml); 4 ml of an aqueous (distilled deionized) solution of $MgSO_4.7H_2O$ (0.29 g/ml); 7.2 g of glucose; and, 2 liters of aqueous (distilled deionized) solution containing NaCl (28 g), $NaHCO_2$ (8.4 g), KCl (1.4 g) and $KH_2PO_4$ (0.6 g).

2. Preparation of Atria

Male albino guinea pigs (400–700 g, preferably 500–600 g) are killed by a blow to the back of the head and exsanguinated by cutting jugular veins and carotid arteries. The thoracic skin is opened from this neck cut and the rib cage exposed. Both sides of the rib cage and the diaphragm are cut and laid back, exposing the heart. The heart is removed by cutting through the vessels above and behind it while it is slightly elevated with forceps holding the ventricle tip. The heart is immediately placed in warm, aerated buffer and further dissected in a large petri dish of the same buffer. Since the pericardium is removed, it is possible to slip iris scissors between the atria and ventricles while holding the aorta and vessels with tweezers and cut off the atria. The atria are then dissected from any remaining tissue and vessels and suspended in the bath using small, curved taperpoint needles formed into hooks and tied to an S-shaped hook and the L-shaped lower support with 00 silk.

A Beckman Type 9308 Strain Gauge Coupler connects a Beckman cardiotachometer to a Grass FT03C strain gauge supported in a rack and pinion clamp. The upper hook of the strain gauge is placed in the edge of the left atrium and the lower hook in the tip of the right atrium. The lower support is clamped in a femur clamp and the upper hook is suspended from the strain gauge lug. The strain gauge is raised until the resting tension on the tissue is 1 gram. The tissue is allowed to stabilize for about one hour with several buffer washings and tension adjustments before the addition of the test compounds.

3. Test Procedure

A control dose-response curve using cumulative, approximately tripling doses is obtained in all three running from 0.1 to 30.0 µM histamine (0.1, 0.3, 1.0, 3.0, etc.) In order to minimize volume changes when adding drugs to the bath, small volumes of concentrated solutions are used. It is convenient to make up a 0.5M solution and dilute it to give 50, 5 and 0.5 mM solutions.

Data recorded consists of the initial baseline rate and the stable plateau rate after each addition. Histamine is then washed out and the tissues are allowed to stabilize again near the initial baseline rate; this may take several rinses and 1 hr. The test compound is then added at the same cumulative doses and rates again recorded. If the compound behaves as an agonist and stimulates, then the dose is increased until the rate plateaus or the concentration is 1.0 mM. If, however, no agonistic activity is observed when the concentrations has reached 100 µM then its antagonistic activity is assessed by repeating the histamine curve without washing out the test compound. Reversibility of effect is assessed by attempting to wash out the test compound and/or histamine and repeat the histamine curve. Erratic or irregular beating or any other abnormal behavior at any time is noted. Calculations consist of the change in rate from base line and that change as a percentage of the maximum rate obtained in the initial control curve. The mean of those percentages ($\pm$SEM) is plotted as a function of agonist concentration (either histamine or test compound) to evaluate the type of response.

B. Lumen Perfused Rat Stomach—Effect on the Gastric Secretion

Male Sprague-Dawley rats weighing between 350 and 500 gm are housed individually according to standard animal husbandry procedures and are deprived of food twenty-four hours prior to testing. The rats are anesthetized by an intraperitoneal injection of 25% solution of urethane (0.5 to 0.7 ml/100 g of body weight). Once anesthetized, the trachea is exposed and cannulated with PE 100 tubing. The jugular vein is exposed and cannulated with PE 50 tubing bevelled at the tip. The abdomen is opened through a midline incision, and the esophagus is isolated excluding the vagus nerve. PE 190 tubing, with a flange on one end, is passed down the rat's mouth through the esophagus and into the stomach. The esophagus is tied off and the tubing checked to make sure that it is securely in the stomach. The duodenum is then identified and a small cut made about 1 cm below the pyloric sphincter. A piece of PE 320 tubing (flanged at one end) is inserted through the cut and into the stomach. It is secured firmly by tying a ligature around the pylorus. Using a 50 ml syringe, the stomach is flushed out with 0.4 mM NaOH through the esophageal tube until the perfusate emerging from the pyloric tube is clear. The animal is placed on a tilted table covered with a Gordon-Rupp water blanket Model 'K' to maintain the rat's body temperature at 30° C. The tube going into the esophagus is attached to a Sage Peristaltic Pump and 0.4 mN NaOH (pH~10.0) is perfused and collected in 30 ml beakers. The beakers are changed every 10 or 15 minutes and the pH of these samples are recorded. Once the pH has stabilized around 6.5–7.5, drugs that affect gastric secretion are given intravenously. The effectiveness of a compound is based on its ability to prevent a drop in pH initiated by a gastric stimulant, such as histamine. See, Ghosh, M. N. and Schild, H. O., *Brit. J. Pharmacol.*, 13: 54 (1958).

The compounds of Formula I have also been determined to exhibit cytoprotective activity.

The cytoprotective effectiveness of the compounds of Formula I is evaluated according to the following test procedure described by Correll, T., "Interaction of Salicylates and other Non-steroidal Anti-inflammatory Agents in Rats as Shown by Gastro-ulcerogenic and Anti-inflammatory Activities, and Plasma Concentrations", Acta. Pharmacology et. Toxicology, 45, 225–231 (1979).

Male Sprague-Dawley rats 140–170 g are housed according to standard animal husbandry procedures. The rats are fasted twenty-four hours prior to testing. On the test day, rats are divided into groups of 5 or 10, with one group serving as controls and receiving vehicle (distilled water or a 0.1% Tween 80 solution). The test compounds, using logarithmic doses, are administered at a dose volume of 10 ml/kg. One hour post-drug, the rats are orally administered (10 ml/kg) aspirin suspended in 0.1% Tween 80 at a dose of 150.0 mg/kg, 1 ml of absolute alcohol, 0.2N NaOH (1 ml) or 0.6N HCl (1 ml), regardless of body weight. Ten minutes after administration animals are sacrificed by cervical dislocation, their stomachs are removed, opened along the greater curvature, rinsed under running tap water and examined for lesions with a 10X magnifying glass.

Data are expressed as an ulcer index which is the sum of the mean number of gastric lesions and the mean lesion severity score. Lesion severity was obtained by determination of the size of the largest lesion as follows:

a. punctate—1
b. $\leq 0.5$ mm $\times$ 1–5 mm—2
c. $\leq 0.5$ mm $\times$ 6–10 mm—3
d. 0.5–1 MM $\times$ 1–5 MM—4
e. 0.5–1 mm $\times$ 6–10 mm—5
f. $>1$ mm or $>10$ mm—6
g. No lesions—0

The reduction of lesion count, lesion severity score and ulcer index as compared to similar measurements made in the controls was expressed as a percentage. Measurement of statistical significance of the results was done by standard methods.

The average ulcer severity ($\pm$S.E.) for each group of animals is calculated. The percent inhibition for each test compound is calculated as follows:

$$\% \text{ inhibition} = \frac{\text{Mean value for control} - \text{Mean value for experimental}}{\text{Mean value for control}} \times 100$$

The results of the anti-secretory and cytoprotective assays, detailed above, establish the anti-secretory activity as H₂-receptor antagonists, the cytoprotective activity, and the utility of the compounds of the present invention in the treatment of peptic ulcers in mammals, including humans. These compounds both aid in the healing of such ulcers and also prevent their formation.

A preferred cytoprotective compound is 1-cyano-3-[3-(5-isoquinolyloxy)isopropyl]-2-methylpseudothiourea which is 100% effective in the above described cytoprotective tests at doses of less than 25 mg/kg.

Other preferred cytoprotective compounds include 2-cyano-1-[3-(5-isoquinolyloxy)propyl]-3-methylguanidine and 5-(3-aminopropoxy)isoquinoline.

A preferred H₂-antagonist compound is 3-amino-4-3-[5-(2-methyl-1,2,3,4-tetrahydroisoquinolyloxy)]-propylamino-1,2,5-thiadiazole-1-oxide.

In particular, the compounds according to Formulae I to V are useful: in the treatment and prevention of hyperacidity and gastrointestinal ulceration; for decreasing gastrointestinal acid secretion in mammals; for stimulating the production of cytoprotective prostaglandins in the gastrointestinal systems of humans and other mammals; and for enhancing the gastrointestinal resistance to gastrointestinal irritants in humans and other mammals.

For all these purposes, the compounds of this invention can be normally administered orally or parenterally. Oral administration is preferred.

The compounds according to the invention, preferably in the form of a salt, may be formulated for administration in any convenient way, and the invention includes within its scope pharmaceutical compositions containing at least one compound according to the invention adapted for use in human or veterinary medicine. Such compositions may be formulated in a conventional manner using one or more pharmaceutically acceptable carriers or excipients. Such compositions may also contain if required other active ingredients, for example, H₁-antagonists, or known antacids such as aluminum hydroxide, magnesium hydroxide, magnesium trisilicate, aluminum glycinate, or calcium carbonate. Suitable carriers include diluents or fillers, sterile aqueous media and various non-toxic organic solvents. The compositions may be formulated in the form of tablets, capsules, lozenges, troches, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers. Where aqueous suspensions for oral use are formulated, the carrier can be emulsifying or suspending agents. Diluents such as ethanol, propylene glycol, glycerin and chloroform and their combinations can be employed as well as other materials.

For parenteral administration, solutions or suspensions of these compounds in sesame or peanut oil or aqueous propylene glycol solutions, as well as sterile aqueous solutions of the soluble pharmaceutically acceptable salts described herein can be employed. Solutions of the salts of these compounds are especially suited for intramuscular and subcutaneous injection purposes. The aqueous solutions, including those of the salts dissolved in pure distilled water, are also useful for intravenous injection purposes, provided that their pH is properly adjusted, suitably buffered, and made isotonic with sufficient saline or glucose.

The dosage regimen is carrying out the methods of this invention is that which insures maximum therapeutic response until improvement is obtained and thereafter the minimum effective level which gives relief. Thus, in general, the dosages are those that are therapeutically effective in the treatment of gastrointestinal disease conditions or symptoms, such as duodenal and peptic ulcer. In general, the dose can be between about 0.1 mg/kg and 100 mg/kg (preferably in the range of 1 to 20 mg/kg), bearing in mind, of course, that is selecting the appropriate dosage in any specific case, consideration must be given to the patient's weight, general health, age, and other factors which may influence response to the drug. The daily dose can range from 1 to 4 times a day.

We claim:

1. A compound of the formula

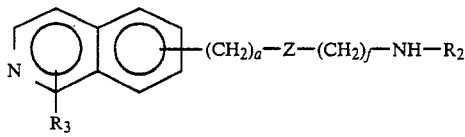

wherein:
Z is O, S,

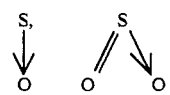

or CH₂;
R₂ is selected from the group consisting of

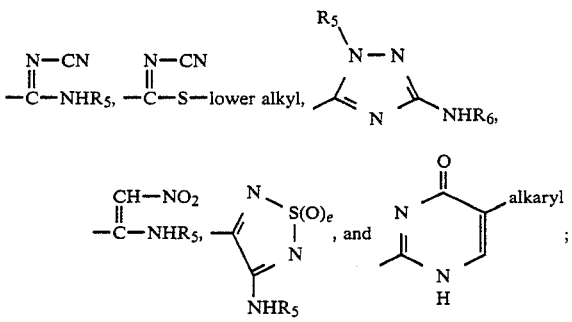

R₃ is hydrogen, lower alkyl, halo, lower alkoxy, hydroxy, hydroxy lower alkyl, halo lower alkyl, amino lower alkyl, mono- or di-loweralkylamino loweralkyl, amino, lower alkylamino, or diloweralkylamino;
R₅ is H or lower alkyl;
R₆ is H, lower alkyl or lower alkanoyl;

and wherein:
a is 0 or 1;
e is 1 or 2;
f is 1, 2, 3 or 4;
or a pharmaceutically acceptable salt thereof.

2. A compound according to the formula

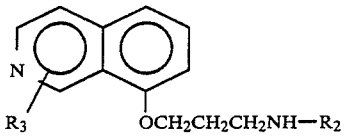

wherein:
R$_2$ is selected from the group consisting of

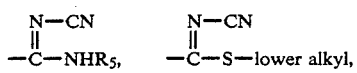

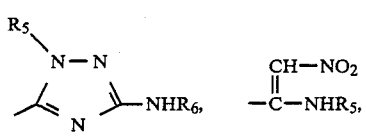

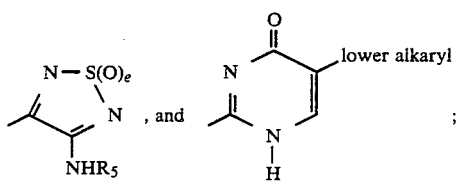

R$_3$ is hydrogen, lower alkyl, halo, lower alkoxy, hydroxy, hydroxy lower alkyl, halo lower alkyl, amino lower alkyl, mono- or di-loweralkylamino lower alkyl, amino, lower alkylamino, or diloweralkylamino;
R$_5$ is H or lower alkyl;
R$_6$ is H, lower alkyl or lower alkanoyl;
e is 1 or 2;
or a pharmaceutically acceptable salt thereof.

3. A compound according to the formula

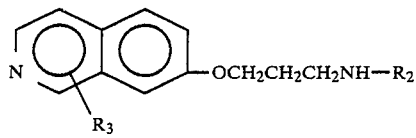

wherein:
R$_2$ is selected from the group consisting of,

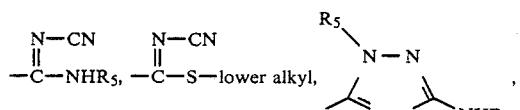 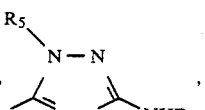

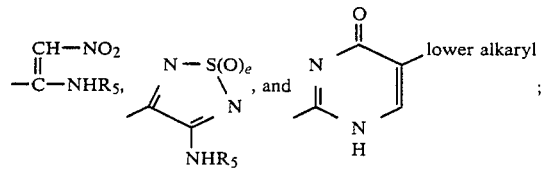

R$_3$ is hydrogen, lower alkyl, halo, lower alkoxy, hydroxy, hydroxy lower alkyl, halo lower alkyl, amino lower alkyl, mono- or di-loweralkylamino lower alkyl, amino, lower alkylamino, or diloweralkylamino;
R$_5$ is H or lower alkyl;
R$_6$ is H, lower alkyl or lower alkanoyl;
e is 1 or 2;
or a pharmaceutically acceptable salt thereof.

4. A compound according to the formula

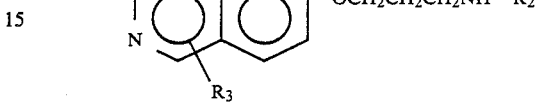

wherein:
R$_2$ is selected from the group consisting of

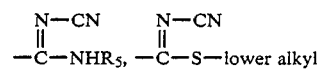

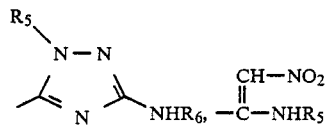

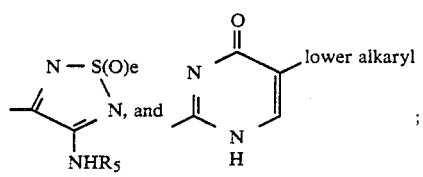

R$_3$ is hydrogen, lower alkyl, halo, lower alkoxy, hydroxy, hydroxy lower alkyl, halo lower alkyl, amino lower alkyl, mono- or di-lower alkylamino lower alkyl, amino, lower alkylamino, or diloweralkylamino;
R$_5$ is H or loweralkyl;
R$_6$ is H, lower alkyl or lower alkanoyl;
e is 1 or 2;
or a pharmaceutically acceptable salt thereof.

5. A compound according to the formula

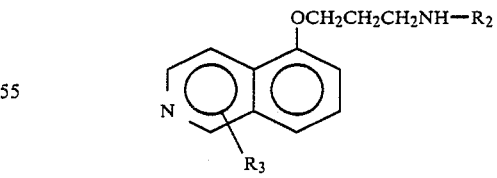

wherein:
R$_2$ is selected from the group consisting of

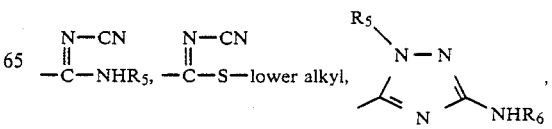 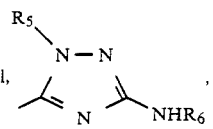

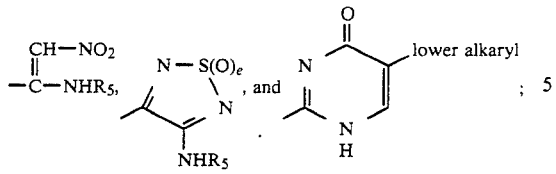

R₃ is hydrogen, lower alkyl, halo, lower alkoxy, hydroxy, hydroxy lower alkyl, halo lower alkyl, amino lower alkyl, mono- or di-loweralkylamino lower alkyl, amino, lower alkylamino, or diloweralkylamino;

R₅ is H or lower alkyl;
R₆ is H, lower alkyl, or lower alkanoyl;
e is 1 or 2;
or a pharmaceutically acceptable salt thereof.

6. 1-cyano-3-[3-(5-isoquinolyloxy)propyl]-2-methyl pseudothiourea or an acid addition salt thereof.

7. 2-cyano-1-[3-(5-isoquinolyloxy)propyl]-3-methyl-guanidine or an acid addition salt thereof.

8. 1-cyano-3-[3-(7-isoquinolyloxy)propyl]-2-methylpseudothiourea or an acid addition salt thereof.

9. 2-cyano-1-(3-(7-isoquinolyloxy)propyl]-3-methyl guanidine or an acid addition salt thereof.

10. A method for decreasing acid secretion in the gastrointestinal tract of mammals by administering thereto an antisecretory effective amount of a compound according to claim 1.

11. A method for the treatment of gastrointestinal hyperacidity and ulceration in a mammal comprising administering thereto an effective amount of a compound according to claim 1.

12. A method for stimulating the production of cytoprotective prostaglandins in the gastrointestinal systems of humans and mammals comprising administering thereto a compound according to claim 1.

13. A method for enhancing the gastrointestinal resistance to gastrointestinal irritants in humans and mammals comprising administering thereto an effective cytoprotective amount of a compound of the formula according to claim 1.

14. A pharmaceutical composition useful for the treatment of gastrointestinal disorders wherein the active ingredient is a compound according to claim 1 in admixture with a pharmaceutical carrier.

15. A method for the treatment of gastrointestinal disorders in a mammal comprising the administration to a mammal suffering from a gastrointestinal disorder an effective gastrointestinal amount of a compound of the formula

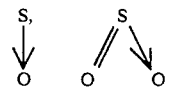

wherein:
Z is O, S,

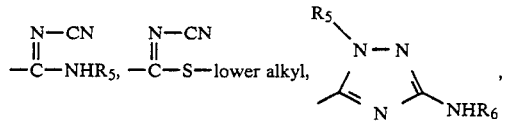

or CH₂;
R₂ is selected from the group consisting of H,

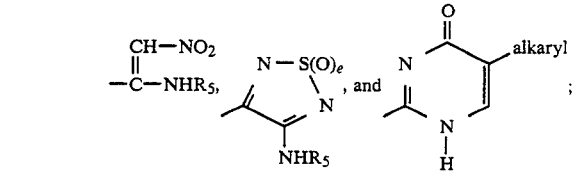

R₃ is hydrogen, lower alkyl, halo, lower alkoxy, hydroxy, hydroxy lower alkyl, halo lower alkyl, amino lower alkyl, mono- or di-loweralkylamino loweralkyl, amino, loweralkylamino, or diloweralkylamino;

R₅ is H or lower alkyl;
R₆ is H, lower alkyl or lower alkanoyl;
and wherein:
a is 0 or 1;
e is 1 or 2;
f is 1, 2, 3 or 4;
or a pharmaceutically acceptable salt thereof.

16. A method according to claim 15 wherein said gastrointestinal disorder is gastrointestinal hyperacidity and said effective gastrointestinal amount comprises an effective antisecretory amount.

17. A method according to claim 15 wherein said gastrointestinal disorder comprises a lowered resistance to gastrointestinal irritation and said effective gastrointestinal amount comprises an effective cytoprotective amount.

* * * * *